United States Patent [19]

Bartels

[11] Patent Number: 4,992,176

[45] Date of Patent: Feb. 12, 1991

[54] DEHYDRATION OF ORGANIC OXYGENATES

[75] Inventor: Craig R. Bartels, Wappingers Falls, N.Y.

[73] Assignee: Texaco Inc., White Plains, N.Y.

[21] Appl. No.: 425,156

[22] Filed: Oct. 23, 1989

[51] Int. Cl.$^5$ .............................................. B01D 61/36
[52] U.S. Cl. .................................. 210/640; 210/654; 210/500.37
[58] Field of Search ........ 210/634, 640, 644, 649–654, 210/500.1, 500.21, 500.27, 500.37; 55/158, 16

[56] References Cited

U.S. PATENT DOCUMENTS

| | | | |
|---|---|---|---|
| 4,444,571 | 4/1984 | Matson | 55/16 |
| 4,466,202 | 8/1984 | Merten | 55/158 |
| 4,627,859 | 12/1986 | Zupancic et al. | 55/158 |

*Primary Examiner*—Frank Sever
*Attorney, Agent, or Firm*—Robert A. Kulason; James J. O'Loughlin; Carl G. Seutter

[57] ABSTRACT

Concentration of aqueous solutions of isopropanol may be effected by a composite membrane including a dibromobutane cross-linked poly(4-vinyl pyridine) bonded to a porous layer of polyacrylonitrile on a polyester backing.

21 Claims, No Drawings

DEHYDRATION OF ORGANIC OXYGENATES

FIELD OF THE INVENTION

This invention relates to the dehydration of organic oxygenates such as isopropyl alcohol or ethylene glycol. More particularly it relates to a membrane technique for effecting separation of water from an aqueous mixture containing isopropyl alcohol or ethylene glycol.

BACKGROUND OF THE INVENTION

As well known to those skilled in the art, it is possible to remove water from mixtures thereof with organic liquids by various techniques including adsorption or distillation. These conventional process, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, would require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the saturated vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyethylene | Cabasso, Korngold & Liu J. Pol. Sc: Letters, 23, 57 (1985) |
| Fluorinated polyether or Carboxylic Acid fluorides | USP 4,526,948 to Dupont as assignee of Resnickto |
| Selemion AMV brand of Asahi Glass | Wentzlaff Boddeker & Hattanbach J. Memb. Sci. 22,333 (1985) |
| cross-linked styrene butadiene (with quaternary ammonium residues on a polyvinyl chloride backing) | |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22, 2159 (1984) |
| Dextrine isophorone diisocyanate | Chem. Econ. Eng. Rev., 17, 34 (1985) |

The cost effectiveness of a membrane is determined by the selectivity and productivity. Of the membrane commercially available, an illustrative polyvinyl alcohol membrane of high performance is that disclosed in European Pat. No. 0 096 339 A2 of GFT as assignee of Bruschke—published 21 Dec. 1983.

European Pat. No. 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

U.S. Pat. No. 4,728,429 to Cabasso et al, U.S. Pat. No. 4,067,805 to Chiang et al, U.S. Pat. No. 4,526,948 to Resnick, U.S. Pat. No. 3,750,735 to Chiang et al, and U.S. Pat. No. 4,690,766 to Linder et al provide additional background.

Additional prior art which may be of interest includes:

*Mobility of Spin Probes in Quaternized Poly(4-Vinylpyridine) Membranes*, Makino, Hamada, and Iijima, in Polym. J. (Toyko), 19(6), 737–45, 1987.

*Effect of Quaternization on the Pervaporation Rate of Water Through Poly(4-Vinylpyridine) Membrane*, Hamaya, and Yamada, in Kobunshi Ronbunshu, 34(7), 545–7, 1977.

*Preparation of Separation Membranes*, Yamamoto, Toi, and Mishima, patent #JP 61/161109 A2, Jul 21 1986. (Japanese).

*Separation of Some Aqueous Amine Solutions by Pervaporation through Poly(4-Vinylpyridine) Membrane* Yamada and Hamaya, in Kobunshi Ronbunshu, 39(6), 407–14, 1982.

*Complex Formation of Crosslinked Poly(4-Vinylpyridine) Resins with Copper (II)*, by Nishide, Deguchi, and Tsuchida, in Bulletin of the Chemical Society of Japan, Vol. (12), 3498–3501 (1976).

It is an object of this invention to provide a novel process for separation of water from organic oxygenates such as isopropyl alcohol. Other objects will be apparent to those skilled in the art.

STATEMENT OF THE INVENTION

In accordance with certain of its aspects, this invention is directed to a method of concentrating a charge aqueous solution of an organic oxygenate which comprises maintaining a non-porous separating layer of poly(vinyl pyridine) which has been cross-linked with an aliphatic polyhalide;

maintaining a pressure drop across said non-porous separating layer of poly(vinyl pyridine);

passing a charge aqueous solution of an organic oxygenate into contact with the high pressure side of said non-porous separating layer whereby at least a portion of said water in said charge aqueous solution and a lesser portion of organic oxygenate in said charge aqueous solution pass by pervaporation through said non-porous separating layer as a lean mixture containing more water and less organic oxygenate than are present in said charge aqueous solution and said charge aqueous solution is converted to a rich liquid containing less water and more organic oxygenate than are present in said charge aqueous solution;

recovering as permeate from the low pressure side of said non-porous separating layer said lean mixture containing more water and less organic oxygenate than are present in said charge aqueous solution, said lean mixture being recovered in vapor phase at a pressure below the vapor pressure thereof; and recovering as retentate from the high pressure side of said non-porous separating layer said rich liquid containing a lower water content and a higher organic oxygenate content than are present in said charge aqueous solution.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven or woven fibrous polyester.

One typical non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @ 0.5 inches of water.

THE POROUS SUPPORT LAYER

The porous support layer of this invention is preferably formed of a sheet or membrane of polyvinylidene fluoride, a teflon polyfluoroethylene polymer, or more preferably of polyacrylonitrile. Typically the support layer may be of thickness of 40–80 microns, say 50 microns and of molecular weight $M_n$ of 5,000–100,000, preferably 20,000–60,000 say 40,000. The polyacrylonitrile is preferably characterized by a pore size of less than about 500A and typically about 200A. This corresponds to a molecular weight cut-off of less than about 100,000, typically about 20,000.

A preferred porous support layer may be the Daicel DUY-L polyacrylonitrile of 40,000 molecular weight cut-off.

Typically the support layer may be characterized by a molecular weight $M_n$ of 100,000, a $T_m$ of 319° C., a $T_g$ of 85° C., a decomposition temperature of 250° C., a tensile strength at yield of 250–568 MPa, a Linear Thermal Expansion Coefficient of 1.6 $K^{-1}$ (above $T_g$) and of 1.0 $K^{-1}$ (below $T_g$), and Water Absorption (at 21° C. and 65% relative humidity) of 1–2.5%. $T_m$ is the melting point and $T_g$ is the glass transition temperature).

THE SEPARATING LAYER

The separating layer or membrane which permits attainment of separation in accordance with this invention includes a non-porous film of cross-linked poly(vinyl pyridine) of thickness of about 1–10 microns, preferably 1–5 microns, say 3 microns. This layer is formed (preferably by casting) from a poly(vinyl pyridine). Although poly(2-vinyl pyridine) may be employed, the preferred separating layer is prepared from poly(4-vinyl pyridine)—typically the Reilline 4200 brand (of Reilly Tar and Chemical Co) of poly(4-vinyl pyridine) in a 10 w % solution in a suitable alcohol solvent such as methanol.

The membrane may be formed by mixing 0.5–2 parts, say 1 part of the 10%–30%, say 20 w % solution of poly(4-vinyl pyridine) in methanol with 1 part methanol, and 0.1–0.8 parts, say 0.52 parts of aliphatic polyhalide cross-linking agent and casting the mixture on a support.

It is a feature of this invention that the separating layer may be a homopolymer or a copolymer of 2-vinyl pyridine or more preferably 4-vinyl pyridine. When copolymers are employed, the co-monomer may be an ethlenically unsaturated monomer, typically vinyl chloride, ethylene, vinyl alcohol, styrene, vinyl acetate, ethylene oxide, or acetonitrile etc. In the preferred embodiment, the separating layer is a homopolymer of 4-vinyl pyridine of molecular weight $M_v$ of 10,000–500,000, preferably 100,000–300,000, say about 200,000.

The polymer may be cross-linked with a cross-linking agent to form the membranes useful in practice of this invention.

Typically the cross-linking agents may contain an aliphatic moiety, preferably containing 2–12 carbon atoms, typically 3–6 carbon atoms, say 4 carbon atoms. Although the cross-linking agent may be a polyhalide, it typically contains 2–5 halogen atoms, most preferably 2. The halogen is preferably bromine or less preferably chlorine or iodine. The halides may preferably be alpha, omega dihalides of linear straight chain aliphatic hydrocarbon. Typical cross-linking agents may be as tabulated infra, the first listed being preferred:

TABLE 1,4-dibromo-n-butane (DBB)
1,5-dibromo-n-pentane (DBP)
1,3-dibromo propane
1,6-dibromo hexane
1,8-dibromo octane 1,4-dichloro-n-butane In situ cross-linking may be carried out by casting onto the preferred polyacrylonitrile support the poly(4-vinyl pyridine) typically in the solution in methanol to which is added the cross-linking agent (typically 1,4-dibromobutane) in mole ratio of cross-linking agent to polymer of 0.2–2, say about 1.13.

It may be possible in one embodiment to cross-link the poly(4-vinyl pyridine) separating layer in one step by casting the solution of poly(4-vinyl pyridine) and polyhalide, followed by heat curing the cast membrane at 100° C.–200°C., say 125° C. for 1–30 minutes, say 2 minutes.

In another embodiment, it may be possible to apply to the porous support layer, a solution of poly(4-vinyl pyridine). This may be dried at 40° C.–80° C., say 50° C. for 2–10 minutes say 4 minutes to form a film. There may then be added onto the surface of this uncross-linked film a solution in methanol containing polyhalide and 2–7w %, say 3.5w % of poly(4-vinyl pyridine).

The composite membrane, whether prepared by the one-step or the two-step process may then be cured in an oven at 100° C.–200° C., say 125° C. for 1–30 minutes, say 2 minutes to yield a film having a thickness of 1–10 microns, say 4 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a porous support layer of preferably polyacrylonitrile of molecular weight $M_n$ of 5,000–100,000, of thickness of 10–80 microns, and of molecular weight cut off of 25,000–100,000 and (iii) as a non-porous separating layer poly(vinyl pyridine) of molecular weight $M_v$ of 10,000–500,000 which has been cross-linked with an aliphatic polyhalide.

The composite membranes of this invention may be utilized in various configurations. It is, for example, possible to utilize the composite in a plate-and-frame configuration in which separating layers may be mounted on the porous support layer with the carrier layer.

It is possible to utilize a spiral mound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the perforations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell(in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the porous support layer of e.g. polyacrylonitrile may be extruded as a fine tube with a wall thickness of typically 0.001–0.1 mm. The extruded tubes are passed through a bath of poly(vinyl pyridine) which is cross-linked and cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter cross-linked and cured in situ prior to mounting in the headers.

PERVAPORATION

It is a feature of the non-porous separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. No. 4,277,344; U.S. Pat. No. 4,039,440; U.S. Pat.

No. 3,926,798; U.S. Pat. No. 3,950,247; U.S. Pat. No. 4,035,291; etc.

It is a feature of the process of this invention that the novel membrane may be particularly useful in pervaporation processes for dewatering aqueous mixtures of organic oxygenates. It may be possible to utilize the process of this invention to remove water from immiscible mixtures therewith as in the case of ethyl acetate (solubility in water at 15° C. of 8.5 parts per 100 parts of water). It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogeneous aqueous solution as is the case for example with isopropanol. The system may also find use in the case of slightly soluble liquids wherein two phases are present (i) water-oxygenate first phase and, as a second phase (ii) either water or oxygenate. Clearly those charge liquids which contain only a small portion of an immiscible second liquid phase may benefit most from the process of this invention. It is also a feature of this invention that it may be particularly useful to separate azeotropes such as isopropanol-water.

The charge organic oxygenates which may be treated by the process of this invention may include alcohols, glycols, weak acids, ethers, esters, ketones, aldehydes, etc. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or glycols (such as ethylene glycol) Results achieved with acids are generally less satisfactory.

Illustrative alcohols may include ethanol, propanol, i-propanol, n-butanol, i-butanol, t-butanol, amyl alcohols, hexyl alcohols, etc.

Illustrative glycols may include ethylene glycol, propylene glycols, butylene glycol or glycol ethers such as diethylene glycol, triethylene glycol, or triols, including glycerine; etc.

Illustrative chlorinated hydrocarbons may include dichloroethane, methylene dichloride, etc.

Illustrative weak acids may include hexanoic acid, octanoic etc. (When acids are present, preferably the pH of the charge liquid should be above about 4. Typical acids which may be treated by the process of this invention include those having a $pKa \leq ca\ 4.8$.

Illustrative esters may include ethyl acetate, methyl acetate, butyl acetate, methyl benzoate, ethylene glycol mono acetate, propylene glycol monostearate, etc.

Illustrative ethers may include tetrahydroforan, diethyl ether, diisopropyl ether, etc.

Illustrative ketones may include acetone, methyl ethyl ketone, acetophenone, etc.

Illustrative aldehydes may include formaldehyde, acetaldehyde, propionaldehyde, etc.

It is believed that the advantages of this invention are most apparent where the organic oxygenate is a liquid which is infinitely miscible with water—typified by isopropyl alcohol or ethylene glycol.

A typical charge may be an aqueous solution containing 70%–95%, say 85 w % isopropanol.

In practice of the pervaporation process of this invention, the charge aqueous organic oxygenate solution typically at 40° C.–120° C., say 80° C. may be passed into contact with the non-porous separating layer of the membrane of this invention. A pressure drop of about one atmosphere is commonly maintained across the membrane Typically, the feed or charge side of the membrane is at about atmospheric pressure and the permeate or discharge side of the membrane is at a pressure of about 2–50 preferably 5–20, say 10 mm. Hg.

The permeate which passes through the membrane includes water and a small proportion of the organic oxygenate from the charge liquid. Typically, the permeate contains 80–99.5, say 98w % water. Permeate is recovered in vapor phase.

Performance is judged by the ability of a membrane system to give a permeate containing decreased content of organic oxygenate (from a charge containing a higher content of organic oxygenate and water) with a good flux (kilograms/meter$^2$-/hour (kmh)) at a predetermined feed temperature and with a vacuum on the permeate side and a condenser (cooled by liquid nitrogen). Compositions falling outside the scope of this invention may be characterized by unsatisfactory separation or unsatisfactory productivity (flux) or both.

Pervaporation may typically be carried out at a flux of 0.6–8.3, say 2.4 gallons per square foot per day which corresponds to about 1–14, say 4 kilograms per square meter per hour (kmh). Typically, the units may show good separation (measured in terms of w % organic oxygenate in the permeate during pervaporation of an aqueous solution of organic oxygenate through a poly(4-vinyl pyridine) separating layer.

It will be noted that as the concentration of the charge increases, the concentration of oxygenate in the permeate increases and the Flux decreases.

Practice of the process of this invention will be apparent to those skilled in the art from inspection of the following examples wherein, as elsewhere in this specification, all parts are parts by weight unless otherwise stated. An asterisk indicates a control example.

Description of Specific Embodiments

EXAMPLE 1

In this example, which represents the best mode presently known of carrying out the process of this invention, the selective separating layer is mounted on the porous support layer of a commercially available (under the trademark DUY-L, from Daicel Corp) composite containing a non-woven polyester backing as carrier layer, bearing as porous support layer, a microporous polyacrylonitrile layer of molecular weight cut-off of 40,000.

The separating layer is formed by applying to the porous support layer, a 10.5w % solution in methanol of poly(4-vinyl pyridine), $M_v$ of about 200,000, available under the trademark Reilline 4200 from Reilly Tar and Chemical Co., to which has been added 20w % of 1,4-dibromobutane (DBB). Mole ratio of cross-linking agent to polymer repeat units is 1.13. The coated support is placed in an oven at 125° C .for 2 minutes to dry and cure the film.

The membrane made by this method is evaluated in a pervaporation cell to which the charge is admitted at 70° C. Permeate pressure is 8 torr at liquid nitrogen temperature.

In this preferred embodiment, the charge solution is an 85.5w % aqueous solution of isopropanol. The permeate condenser contains an aqueous solution containing only 1.4w % isopropanol. The Flux (kmh) is 2.87 kmh.

EXAMPLES 2–33

In this series of Examples, the procedure of Example 1 is generally followed except:

(i) In Examples 7–8, 11–12, 15, 18, 21, and 24–25, the concentration of the poly(4-vinyl pyridine) in methanol is 20w % instead of 10w % as in Example 1.

(ii) In Examples 2–3, 5–25, 29, and 33, the cross-linking agent is DBP (i.e. dibromopentane); and in Example 4, no cross-linking agent is used.

(iii) In Example 2, curing is carried out at 50° C. for 60 minutes; in Example 3, curing is carried out at 125° C. for 5 minutes. In Examples 5–21 and 26–33, curing is carried out at 125° C. for 2 minutes; and in Examples 22–25 curing is carried out at 150° C. for 2 minutes.

(iv) Temperature of pervaporation is 70° C. in Examples 2–12, 16–18, and 22–29, and 80° C. in Examples 13–15, 19–21, and 30–33.

(v) Charge contains isopropanol/water in all cases except that in Examples 16–18 the charge contains ethanol/water; and in Examples 19–21 and 30–33, the charge contains ethylene glycol/water.

The following Table sets forth the mole ratio (MR) of cross-linking agent to polymer; the aqueous feed (isopropanol IPA or ethylene glycol EG or ethanol EtOH); the feed concentration FD CNC w % organic; the permeate concentration PM CNC w % organic; and the Flux in kilograms per square meter per hour (kmh).

TABLE

Support: Daicel DUY-L polyacrylonitrile
Reilline 4200, ca 25% poly(4-vinyl pyridine) solids in MeOH
Coating: 3 mil

| Example | MR | FD | FD CNC % | PM CNC % | FLUX kmh |
|---|---|---|---|---|---|
| 2 | .28 | IPA | 84.4 | 27.7 | 4.49 |
| 3 | .28 | IPA | 84.4 | 19.1 | 3.85 |
| 4 | 0 | IPA | 86.0 | 84.0 | 12.2 |
| 5 | .28 | IPA | 85.8 | 20.1 | 4.55 |
| 6 | .56 | IPA | 85.8 | 3.9 | 3.47 |
| 7 | .28 | IPA | 85.8 | 13.7 | 3.21 |
| 8 | .14 | IPA | 85.8 | 29.9 | 4.70 |
| 9 | .28 | IPA | 94.2 | 52.5 | 4.29 |
| 10 | .56 | IPA | 94.2 | 9.8 | 1.23 |
| 11 | .28 | IPA | 94.2 | 38.7 | 1.94 |
| 12 | .14 | IPA | 94.2 | 74.6 | 9.06 |
| 13 | .28 | IPA | 94.9 | 58.6 | 4.98 |
| 14 | .56 | IPA | 94.9 | 14.3 | 1.21 |
| 15 | .28 | IPA | 94.9 | 46.2 | 2.23 |
| 16 | .28 | EtOH | 90.2 | 71.3 | 11.66 |
| 17 | .56 | EtOH | 90.2 | 50.4 | 4.63 |
| 18 | .28 | EtOH | 90.2 | 66.8 | 5.24 |
| 19 | .28 | EG | 84.7 | 2.1 | 2.43 |
| 20 | .56 | EG | 84.7 | 0.73 | 2.32 |
| 21 | .28 | EG | 84.7 | 0.14 | 1.72 |
| 22 | .28 | IPA | 84.4 | 12.2 | 3.87 |
| 23 | .56 | IPA | 84.4 | 14.3 | 2.46 |
| 24 | .28 | IPA | 84.4 | 23.8 | .52 |
| 25 | .14 | IPA | 84.4 | 79.7 | 3.95 |
| 26 | .28 | IPA | 84.8 | 58.5 | 11.4 |
| 27 | .56 | IPA | 84.8 | 61.3 | 14.5 |
| 28 | .87 | IPA | 84.8 | 6.0 | 4.10 |
| 29 | .56 | IPA | 84.8 | 9.2 | 3.80 |
| 30 | .28 | EG | 85.6 | 42.4 | 1.59 |
| 31 | .56 | EG | 85.6 | 47.7 | 3.11 |
| 32 | .87 | EG | 85.6 | .21 | 1.59 |
| 33 | .56 | EG | 85.6 | 72.0 | 2.61 |

From the above Table (and Example 1) it will be apparent that it is possible to attain permeate containing as little as 3.9 w % isopropanol when charging an 85.5 w % aqueous solution of isopropanol—or alternatively as little as 50.4 w % ethanol when charging a 90.2 w % aqueous solution of ethanol—or as little as 0.14 w % ethylene glycol when charging an 84.7 w % aqueous solution of ethylene glycol.

In control Example 4, no cross-linking agent is employed. The membrane dissolved in the charge and no separation is achieved.

EXAMPLES 34–67

In this series of Examples, the procedure of Example 1 is generally followed. In all examples, the concentration of poly(4-vinyl pyridine) in methanol is 10 w % and curing is carried out at 125° C. for 2 minutes and the feed is aqueous isopropanol IPA and the temperature of separation is 70° C. The cross-linking agent is 1,4-dibromobenzene DBB in all cases except Examples 37, 40, 43, 46, 49, 52, 55, 58, 61, 64, and 67 in which it is 1,5-dibromopentane.

The Table sets forth the mole ratio of cross-linking agent to polymer MR; the concentration of organic in the charge aqueous mixture to separation FD CNC % in weight percent; the concentration of organic in w % in the permeate PM CNC %; and the Flux in kmh.

TABLE

Support: Daicel DUY-L
Reilline 4200, ca 25% poly(4-vinyl pyridine) solids in MeOH
Coating: 3 mil

| Example | MR | FD CNC % | PM CNC % | FLUX kmh |
|---|---|---|---|---|
| 34 | .86 | 85.5 | 75.6 | 1.83 |
| 35 | 1.13 | 85.5 | 1.4 | 2.87 |
| 36 | 1.39 | 85.5 | 6.0 | 2.97 |
| 37 | .81 | 85.5 | 5.1 | 3.18 |
| 38 | 1.13 | 95.3 | 1.7 | .67 |
| 39 | 1.39 | 95.3 | 17.1 | .90 |
| 40 | .81 | 95.3 | 12.5 | .86 |
| 41 | 1.13 | 98.08 | 5.0 | .23 |
| 42 | 1.39 | 98.08 | 39.5 | .47 |
| 43 | .81 | 98.08 | 30.6 | .38 |
| 44 | 1.13 | 98.20 | 5.7 | .15 |
| 45 | 1.39 | 98.20 | 45.4 | .38 |
| 46 | .81 | 98.20 | 35.2 | .30 |
| 47 | 1.13 | 98.47 | 6.2 | .14 |
| 48 | 1.39 | 98.47 | 44.9 | .35 |
| 49 | .81 | 98.47 | 36.5 | .30 |
| 50 | 1.13 | 98.81 | 7.0 | .12 |
| 51 | 1.39 | 98.81 | 48.5 | .34 |
| 52 | .81 | 98.81 | 40.0 | .28 |
| 53 | 1.13 | 98.98 | 8.2 | .10 |
| 54 | 1.39 | 98.98 | 53.0 | .31 |
| 55 | .81 | 98.98 | 43.3 | .25 |
| 56 | 1.13 | 99.56 | 19.6 | .04 |
| 57 | 1.39 | 99.56 | 73.9 | .24 |
| 58 | .81 | 99.56 | 66.0 | .17 |
| 59 | 1.13 | 99.63 | 24.0 | .03 |
| 60 | 1.39 | 99.63 | 77.9 | .22 |
| 61 | .81 | 99.63 | 71.5 | .16 |
| 62 | 1.13 | 99.75 | 29.6 | .016 |
| 63 | 1.39 | 99.75 | 73.9 | .24 |
| 64 | .81 | 99.75 | 66.0 | .17 |
| 65 | 1.13 | 99.75 | 29.6 | .016 |
| 66 | 1.39 | 99.75 | 73.9 | .24 |
| 67 | .81 | 99.75 | 66.0 | .17 |

From the above Table, it may be observed that it is possible to treat e.g. a charge 85.5 w % solution of isopropanol in water by the process of this invention at 70° C. to attain a permeate containing 1.4 w % isopropanol; and this charge can be dehydrated to water concentration of 0.25w % water while maintaining a high flux of 0.17 kmh.

EXAMPLES 68-76

In this series of Examples the effect of temperature on the separation of water/isopropanol is noted. The poly(4-vinyl pyridine) membrane is cast from 10 w % solution in methanol containing cross-linking agent. The cross-linking agent is 1,4-dibromobutane DBB in all Examples except 70, 73, and 76 in which it is 1,5-dibromopentane (DBP).

Curing of the membrane is carried out at 125° C. for 2 minutes. The feed is aqueous isopropanol. The Table shows the mole ratio (MR) of cross-linking agent to polymer; the Feed concentration (FD CNC) of isopropanol in the aqueous solution, the temperature (TMP) ° C. of separation, the concentration (PM CNC) (w %) of isopropanol in the permeate, and the Flux in kmh.

TABLE

Support: Daicel DUY-L
Reilline 4200, ca 25% poly(4-vinyl pyridine) solids in MeOH
Coating: 3 mil

| Example | MR | FD CNC % | TMP % | PM CNC % | FLUX kmh |
|---|---|---|---|---|---|
| 68 | 1.13 | 85.2 | 70 | 0.94 | 1.93 |
| 69 | 1.39 | 85.2 | 70 | 3.87 | 1.74 |
| 70 | .81 | 85.2 | 70 | 3.08 | 1.90 |
| 71 | 1.13 | 85.9 | 60 | 2.00 | 2.10 |
| 72 | 1.39 | 85.9 | 60 | 11.88 | 2.24 |
| 73 | .81 | 85.9 | 60 | 9.00 | 2.32 |
| 74 | 1.13 | 84.6 | 50 | 1.75 | 1.48 |
| 75 | 1.39 | 84.6 | 50 | 9.72 | 1.50 |
| 76 | .81 | 84.6 | 50 | 8.60 | 1.54 |

From the above Table, it is apparent that lowest concentration of isopropanol in the permeate is attained by operation at 70° C. when the mole ratio of cross-linking agent to polymer is 1.13.

EXAMPLES 77-83

In this series of Examples, the membrane is cast as in Examples 68-76 using 1,4-dibromobutane (mole ratio of cross-linking agent to polymer of 1.39) as cross-linking agent. The membrane is cured at 125° C. for 2 minutes. Feed is aqueous ethylene glycol. The Table sets forth the Feed concentration FD CNC in w %, the temperature TMP ° C. of separation, the w % concentration of PM CNC ethylene glycol in the permeate, and the Flux kmh.

TABLE

Support: Daicel DUY-L
Reilline 4200, ca 25% poly(4-vinyl pyridine) solids in MeOH
Coating: 3 mil

| Example | FD CNC % | TMP °C. | PM CNC % | FLUX kmh |
|---|---|---|---|---|
| 77 | 83.0 | 50 | 0.13 | 11.6 |
| 78 | 84.5 | 56 | 0.38 | 0.79 |
| 79 | 85.2 | 50 | 0.20 | 0.65 |
| 80 | 85.1 | 50 | 0.60 | 0.64 |
| 81 | 85.7 | 60 | 0.62 | 0.96 |
| 82 | 85.0 | 70 | 0.20 | 1.38 |
| 83 | 85.3 | 80 | 0.20 | 1.68 |

From this Table, it is apparent that it is possible to treat an aqueous charge containing 83.0 w % ethylene glycol and to obtain a permeate containing only 0.13 w % ethylene glycol at a Flux of 11.6 kmh. This is unexpected. It may be noted that best results (in terms of permeate concentration) are attained at 50° C. The results of Example 77 were obtained at one hour after start-up. All other results in the Table were obtained at least twenty-four hours after start-up.

EXAMPLES 84-86

In this series of examples, the separating membrane is prepared by adding to a 20w % solution of poly(4-vinyl pyridine) in methanol) an equal weight of alcohol cosolvent and 1,4-dibromobutane in mole ratio of 1,4-dibromobutane to polymer repeating unit of 1.13. The curing temperature is as noted in the Table and the curing time is 2 minutes. In all cases the charge liquid contained 85.1 w % isopropanol and 14.9 w % water.

TABLE

| Example | Alcohol Cosolvent | Curing Temp °C. | Feed Conc W % Alcohol | Permeate Conc W % | Flux Kmh |
|---|---|---|---|---|---|
| 84 | Isopropanol | 125 | 85.1 | 3.15 | 6.46 |
| 85 | Isopropanol | 100 | 85.1 | 8.43 | 7.31 |
| 86 | 2-butanol | 100 | 85.1 | 3.64 | 5.90 |

Although this invention has been illustrated by reference to specific embodiments, it will be apparent to those skilled in the art that various charges and modifications may be made which clearly fall within the scope of the invention.

What is claimed:

1. The method of concentrating a charge aqueous solution of an organic oxygenate which comprises
maintaining a non-porous separating layer of a poly(4-vinyl pyridine) which has been cross-linked with an aliphatic polyhalide;
maintaining a pressure drop across said non-porous separating layer of poly(4-vinyl pyridine);
passing a charge aqueous solution of an organic oxygenate into contact with the high pressure side of said non-porous separating layer of poly(4-vinyl pyridine) whereby at least a portion of said water in said charge aqueous solution and a lesser portion of organic oxygenate in said charge aqueous solution pass by pervaporation through said non-porous separating layer as a lean mixture containing more water and less organic oxygenate than are present in said charge aqueous solution and said charge aqueous solution is converted to a rich liquid containing less water and more organic oxygenate than are present in said charge aqueous solution;
recovering as permeate from the low pressure side of said non-porous separating layer, said lean mixture containing more water and less organic oxygenate than are present in said charge aqueous solution, said lean mixture being recovered in vapor phase at a pressure below the vapor pressure thereof; and
recovering as retentate from the high pressure side of said non-porous separating layer said rich liquid containing a lower water content and a higher organic oxygenate content than are present in said charge aqueous solution.

2. The method claimed in claim 1 wherein said non-porous separating layer is a homopolymer of 4-vinyl pyridine.

3. The method claimed in claim 1 wherein said non-porous separating layer is a homopolymer of 4-vinyl pyridine of molecular weight $M_v$ of 100,000-300,000.

4. The method claimed in claim 1 wherein said non-porous separating layer is a copolymer of 4-vinyl pyridine and an ethylenically unsaturated monomer.

5. The method claimed in claim 1 wherein said non-porous separating layer is cross-linked with an aliphatic dihalide.

6. The method claimed in claim 1 wherein said non-porous separating layer is cross-linked with an aliphatic dihalide containing 2-12 carbon atoms.

7. The method claimed in claim 1 wherein said non-porous separating layer is cross-linked with dibromobutane.

8. The method claimed in claim 1 wherein said organic oxygenate is a chlorinated hydrocarbon, alcohol, glycol, weak acid, ester, ether, aldehyde, or ketone.

9. The method claimed in claim 1 wherein said organic oxygenate is an alcohol.

10. The method claimed in claim 1 wherein said organic oxygenate is isopropanol.

11. The method claimed in claim 1 wherein said organic oxygenate is ethanol.

12. The method claimed in claim 1 wherein said organic oxygenate is ethylene glycol.

13. The method claimed in claim 1 wherein said organic oxygenate is at least partially miscible with water.

14. The method claimed in claim 1 wherein said organic oxygenate is infinitely miscible with water.

15. The method claimed in claim 1 wherein said charge is a single phase charge.

16. The method claimed in claim 1 wherein said charge is a two phase charge.

17. The method claimed in claim 1 wherein said separating layer has a thickness of about 1-10 microns.

18. The method claimed in claim 1 wherein said poly(4-vinyl pyridine) which has been cross-linked is supported on a porous support layer.

19. The method in claim 18 wherein said porous support layer is a polyacrylonitrile polymer.

20. The method claimed in claim 18 wherein said porous support layer is a polyacrylonitrile polymer of molecular weight $M_n$ of 5,000-100,000 and of molecular weight cut off of less than about 100,000.

21. The method of concentrating a charge aqueous solution of isopropyl alcohol which comprises
maintaining a non-porous separating layer of cast poly(4-vinyl pyridine) which has been crosslinked with dibromobutane, said separating layer being supported on a porous support layer of polyacrylonitrile;
maintaining a pressure drop across said separating layer and said porous support layer;
passing charge aqueous solution of isopropanol into contact with the high pressure side of said non-porous separating layer whereby at least a portion of the water in said charge aqueous solution and a lesser portion of isopropanol in said charge aqueous solution passes by pervaporation through non-porous separating layer as a lean mixture containing more water and less isopropanol than are present in said charge aqueous solution and said charge aqueous solution is converted to a rich liquid containing less water and more isopropanol than are present in said charge aqueous solution;
recovering as permeate from the low pressure side of said non-porous separating layer said lean mixture containing more water and less isopropanol than are present in said charge aqueous solution, said lean mixture being recovered in vapor phase at a pressure below the vapor pressure thereof; and
recovering as retentate from the high pressure side of said non-porous separating layer said rich liquid containing a lower water content and a higher isopropanol content than are present in said charge aqueous solution.

* * * * *

UNITED STATES PATENT AND TRADEMARK OFFICE
CERTIFICATE OF CORRECTION

PATENT NO. : 4,992,176
DATED : February 12, 1991
INVENTOR(S) : Craig R. Bartels

It is certified that error appears in the above-identified patent and that said Letters Patent is hereby corrected as shown below:

Col 4, line 25, after "pyridine)" insert -- solution --

Claim 1, column 12, line 32, 34 and 38, cancel "4-"

Claim 18, column 13, line 33, cancel "4-"

Signed and Sealed this

Twelfth Day of October, 1993

Attest:

BRUCE LEHMAN

Attesting Officer

Commissioner of Patents and Trademarks